United States Patent [19]

Hideshima

[11] Patent Number: 5,042,484

[45] Date of Patent: Aug. 27, 1991

[54] AIR PUFF TYPE TONOMETER

[75] Inventor: Masayuki Hideshima, Tokyo, Japan

[73] Assignee: Kabushiki Kaisha Topcon, Tokyo, Japan

[21] Appl. No.: 257,368

[22] Filed: Oct. 13, 1988

[30] Foreign Application Priority Data

Oct. 13, 1987 [JP] Japan .................................. 62-258049

[51] Int. Cl.⁵ .............................................. A61B 3/16
[52] U.S. Cl. .................................... 128/648; 128/645; 128/652
[58] Field of Search ................................ 128/648–652, 128/745; 73/81; 341/139, 122

[56] References Cited

U.S. PATENT DOCUMENTS

| 3,783,247 | 1/1974 | Klein | 341/122 |
|---|---|---|---|
| 4,131,113 | 12/1978 | Fender et al. | 128/745 |
| 4,164,863 | 8/1979 | Ragsdale | 128/652 |
| 4,747,296 | 5/1988 | Feldon et al. | 128/652 |
| 4,817,620 | 4/1989 | Katsuragi | 128/648 |
| 4,827,191 | 5/1989 | Chapman | 341/139 |
| 4,834,105 | 5/1989 | Mathews et al. | 128/648 |

*Primary Examiner*—Lee S. Cohen
*Assistant Examiner*—John D. Zele
*Attorney, Agent, or Firm*—Finnegan, Henderson, Farabow, Garrett & Dunner

[57] ABSTRACT

An air puff type tonometer having a source for projecting a light beam toward the cornea of an eye to be tested, an alignment sensor for receiving the light beam after reflection from the cornea and providing a corresponding received light signal, a device for detecting optical alignment based on the received light signal, a device for directing an air puff, a device for providing an applanation signal corresponding to the applanation state of the cornea when the cornea is applanated by an air puff upon the cornea, an A/D converter for converting the applanation signal in accordance with a preset comparison reference value, and a device for setting the comparison reference value based on quantity of light received by the alignment sensor.

10 Claims, 6 Drawing Sheets

AIR PUFF TYPE TONOMETER

BACKGROUND OF THE INVENTION

A. Field of the Invention

This invention relates to an air puff type tonometer for detecting an applanation (flat) state of the cornea of an eye by utilizing a detection light beam that is reflected from the cornea, and measuring the eye pressure by detecting the pressure of the air puff when the applanation state of the cornea is detected.

B. Description of the Prior Art

In a conventional air puff type tonometer, an air puff is directed at the cornea of an eye to be tested and at the same time a detection light beam is projected toward the cornea from a light source. When the detection light beam is reflected from the cornea, the reflected light beam is received by a light receiving device. The applanation state of the cornea is detected based on the quantity of the light received by the light receiving device. In the conventional tonometer, the quantity of light provided from the light source and the detection sensitivity of the applanation detecting system are set constant, because the reflectance of the cornea of the eye to be tested, when the applanation is obtained, is presumed constant.

However, in practice, the reflectance of the cornea may be different from one individual to another. Particularly, when the outer surface of the cornea is not smooth, the reflectance of such cornea can be as small as ¼ to 1/5 times that of a smooth cornea outer surface.

Therefore, if the detecting sensitivity of the applanation detecting system is adjusted for an eye with a maximum reflectance, the detecting system would not work well for an eye with a minimum reflectance because the detection signal provided from the applanation detecting system becomes too small for an accurate detection of the applanation. On the other hand, if the detecting sensitivity is adjusted for an eye with the minimum reflectance, the applanation detecting system would be saturated if the detection were made for an eye with the maximum reflectance, thus making it impossible to detect the applanation state of the cornea.

SUMMARY OF THE INVENTION

An object of the present invention is to provide an air puff type tonometer which is capable of measuring the eye pressure with high accuracy irrespective of the reflectance of the cornea of an eye to be tested.

Another object of the present invention is to provide an air puff type tonometer which is not adversely affected by noise.

In the air puff type tonometer according to the present invention, a light source provides a light beam and projects it toward the cornea of an eye to be tested. An alignment sensor receives the light beam after it is reflected from the cornea, and provides a corresponding received light signal. An alignment detecting device detects optical alignment based on the received light signal. An applanation detecting device provides an applanation signal corresponding to an applanated state of the cornea when the cornea is applanated by directing an air puff at the cornea. An A/D converter converts the applanation signal based on a comparison reference value. The air puff type tonometer includes a device for setting the comparison reference value based on the quantity of light received by the alignment sensor.

In an embodiment of the present invention, the comparison reference value setting devices includes an A/D converter which converts the received light signal into a corresponding digital signal, and a D/A converter which converts the digital signal into a corresponding analog signal when the alignment detecting device detects an alignment.

DETAILED DESCRIPTION OF THE EMBODIMENTS

Several embodiments of the present invention will be described with reference to the accompanying drawings.

Figure 1:
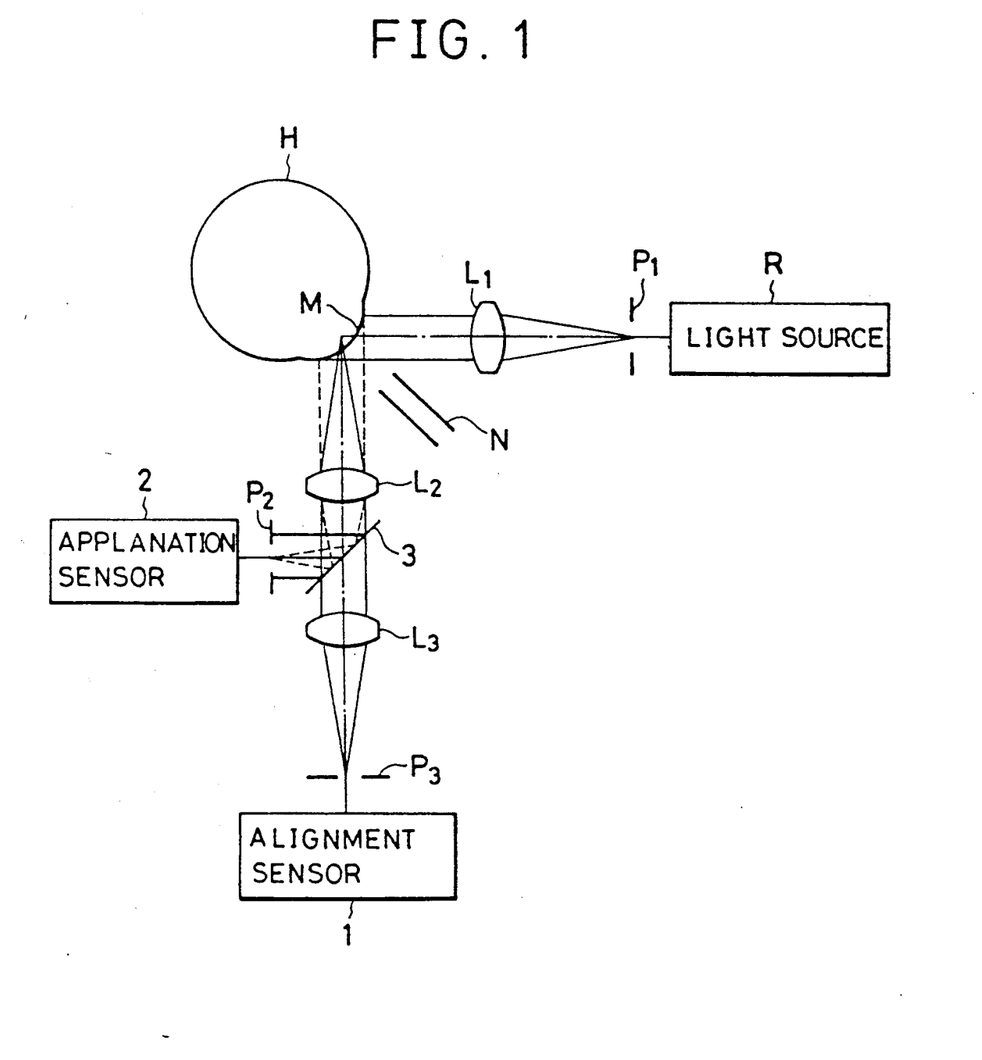
FIGS. 1 and 2 are a schematic view showing the arrangement of optical systems of an air puff type tonometer according to the present invention.
Figure 2:
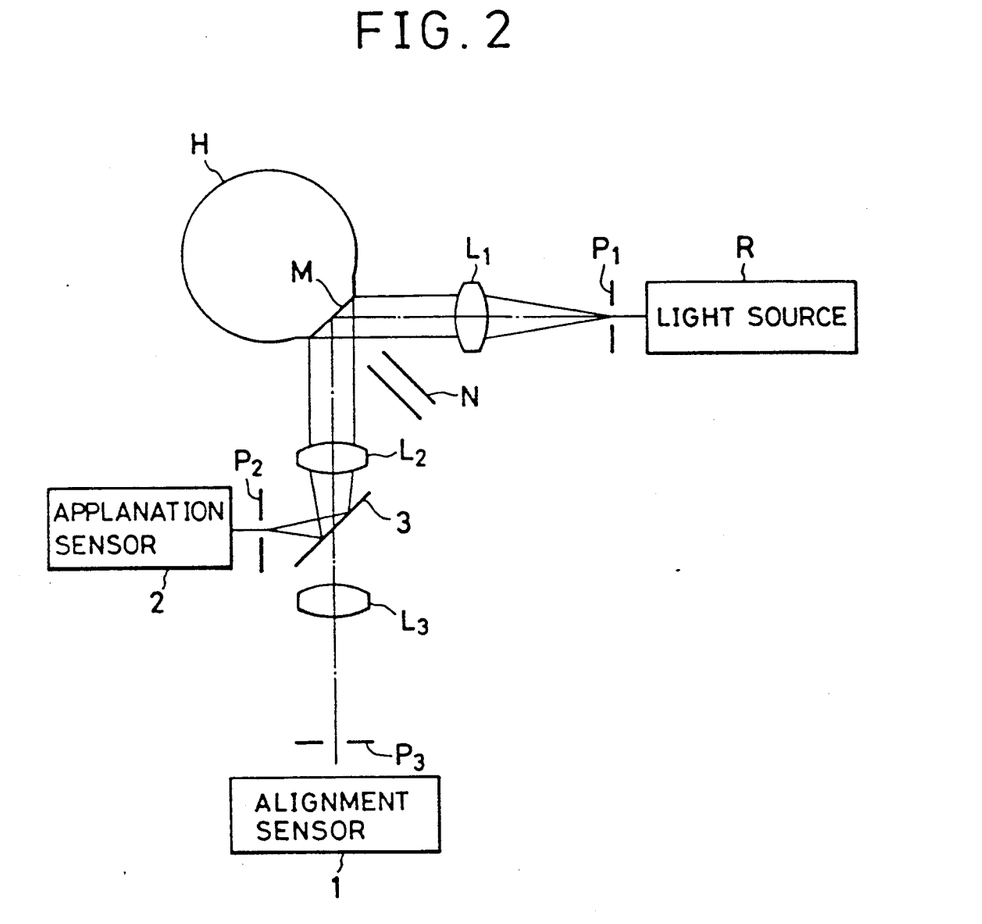

FIGS. 1 and 2 are a schematic view showing the arrangement of optical systems of the air puff type tonometer of the present invention. In the figures, a light source R provides a light beam directed through target mark or diaphragm $P_1$ toward an eye H to be tested. The projected light beam is split into several parallel light beams by a lens $L_1$ and projected to a cornea M of eye H. Since cornea M functions like a convex mirror, the virtual image formed of diaphragm $P_1$ is formed at the rear part of the cornea M. Lenses $L_2$ and $L_3$ are arranged such that the virtual image is formed on a diaphragm $P_3$. An alignment sensor 1 provides an alignment completion signal when the image formed of diaphragm $P_1$ is formed on diaphragm $P_3$ when a nozzle N and cornea M are aligned. Usually, a plurality of such alignment systems are provided to improve detection accuracy or to display displacing direction. However, the detailed description will be omitted here.

In FIG. 2, when cornea M is applanated by an air puff from nozzle N, the image formed of diaphragm $P_1$ is formed on diaphragm $P_3$ through partially-reflective mirror 3; and a greater portion of projected light is received by an applanation sensor 2 than prior to applanation. Applanation sensor 2 detects the applanation state of cornea M based on the received quantity of light, and the pressure of the air puff, when this applanation is detected, is detected to be the eye pressure of eye H.

Figure 3:
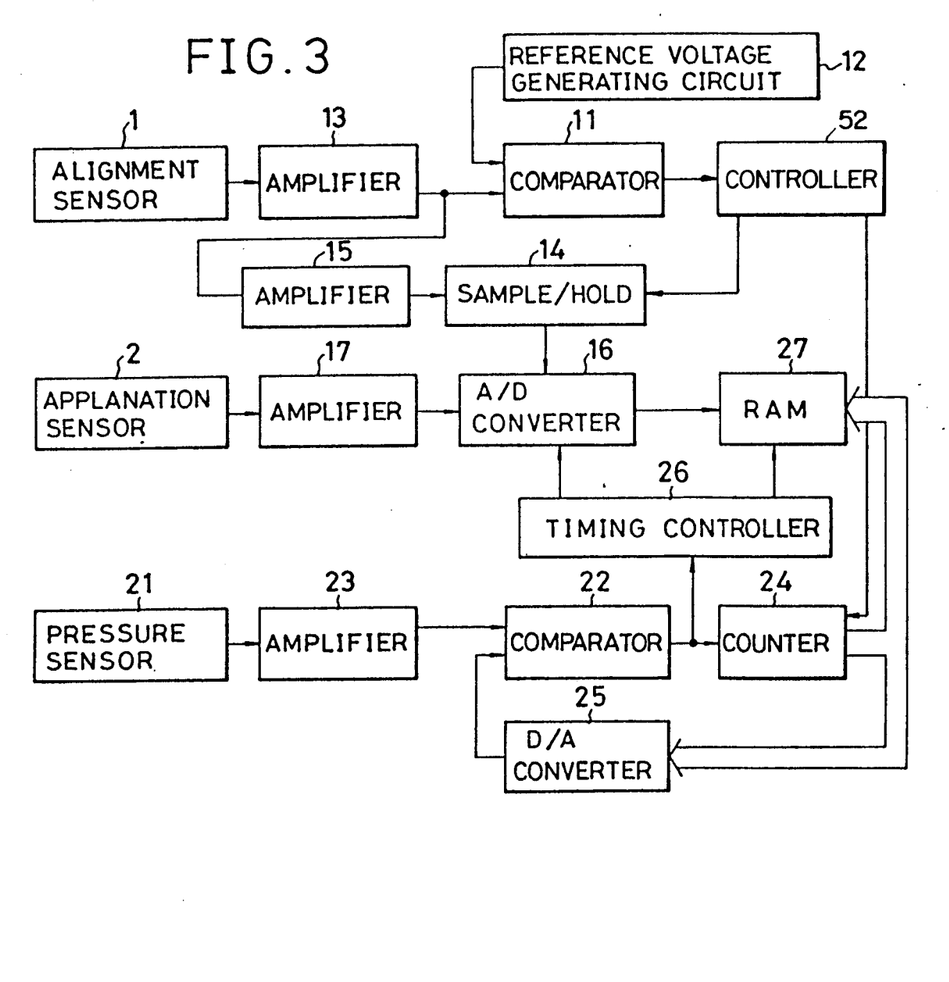
FIG. 3 is a block diagram showing a signal processing system according to a first embodiment of the present invention.

FIG. 3 is a block diagram showing the signal processing system of the air puff type tonometer according to a first embodiment of the present invention. A comparator 11 compares a reference voltage, which is provided from a reference voltage generating circuit 12, with a received light signal which is provided through an amplifier 13, from alignment sensor 1 and provides an alignment completion signal when the received light signal voltage is greater than or equal to the reference voltage. Sample-hold circuit 14 samples and holds the received light signal when the alignment is completed. An amplifier 15 couples the output power of amplifier 13 to sample-hold circuit 14. An alignment detecting system comprises alignment sensor 1, comparator 11, reference voltage generating circuit 12, sample-hold circuit 14, and amplifiers 13 and 15.

Sample-hold circuit 14 provides a comparison reference voltage to an A/D converter 16, which in turn converts the applanation signal provided from applanation sensor 2, through an amplifier 17, to a digital signal in accordance with the comparison reference voltage and a command signal provided from a timing controller 26.

The voltage range of the applanation signal provided to A/D converter 16, is controlled by the comparison reference voltage. For example, when the input voltage provided from applanation sensor 2 to A/D converter 16 is large enough to saturate A/D converter 16, the comparison reference voltage is adjusted to be high such that the coefficient of conversion is reduced and the converted digital signal provided from A/D converter 16 has a predetermined voltage range. On the other hand, when the input voltage is small, the comparison reference voltage is adjusted to be low such that the coefficient of conversion is increased and the converted digital signal has the same predetermined range. Therefore, since the input voltage is controlled in accordance with the comparison reference voltage, the converted digital signal having substantially the same predetermined voltage range is always obtained for accurate measurement of the eye pressure.

A pressure sensor 21 detects the pressure of the air puff jetted from nozzle N. A comparator 22 compares a corresponding pressure signal, provided from pressure sensor 21 through an amplifier 23, with an analog count signal provided from a D/A converter 25. The count analog signal is obtained by converting a count number provided from a counter 24. Comparator 22 provides a high voltage level (H-level) signal when the pressure signal voltage is greater than the count analog signal, and provides a relatively lower voltage level (L-level) signal when the pressure signal voltage is less than the count analog signal value.

Timing controller 26 provides the command signal for activating A/D converter 16 when comparator 22 provides the H-level signal, and provides control for storing the converted digital signal in a RAM 27. Counter 24 increments the count number by unity every time the voltage level provided from comparator 22 is changed from the L-level to the H-level. RAM 27 stores the converted digital signal in a designated address. The designated address in RAM 27 corresponds to the incremented count number.

In other words, comparator 22 compares the count analog signal with the pressure signal provided from pressure sensor 21. When the pressure signal is greater than the count analog signal, the output of comparator 22 is changed to the H-level signal from the L-level and the count number of counter 24 is incremented, the count analog signal, which is provided from D/A converter 25, is accordingly increased by a certain voltage portion.

If the increased voltage portion is preset to a constant value, such that the analog count signal is greater than the pressure signal, comparator 22 will be changed from the H-level to the L-level. Since this process repeats in a loop comprising comparator 22, counter 24 and D/A converter 25, the count number of counter 24 is increased as the pressure of the air puff is increased, and a corresponding count number is provided from counter 24. Since the count number designates the address of RAM 17, the address and the pressure of the air puff corresponds to one another.

The operation of the air puff type tonometer will now be described.

The detection light beam is provided from light source R. Then, the optical systems are aligned with respect to cornea M of eye H to be tested. Upon completion of the alignment, an alignment completion signal is provided by comparator 11. In response to the alignment completion signal, a controller 52 activates sample-hold circuit 14 and sets counter 24 to an initial zero value. Sample-hold circuit 14 holds the applanation signal provided from alignment sensor 1, when the optical alignment is completed, through amplifiers 13 and 15. Immediately thereafter, the air puff if directed from nozzle N toward cornea M.

Pressure sensor 21 provides a pressure signal having a value corresponding to the pressure of the air puff, and comparator 22 compares this pressure signal with the count analog signal provided from D/A converter 25. Since the count number of counter 24 is set to zero and the count analog signal has a value corresponding the zero count number, the pressure signal value is greater than the count analog signal. As a result, the output of comparator 22 is changed to the H-level from the L-level and the count number of counter 24 is incremented by unity.

A signal corresponding to the incremented count number is converted to the count analog signal by D/A converter 25 for comparison with the pressure signal by comparator 22 whereby the counter analog signal voltage is increased in response to the incremented count number. If the increased portion of the count analog signal is preset such that the increased portion is greater than the increase in the pressure of the air puff, the count analog signal will be greater than the pressure signal and the output of the comparator 22 will be changed to the L-level from the H-level. The pressure of the air puff is gradually increased with time, and the count number is incremented by unity every time the pressure signal is greater than the count analog signal.

When cornea M is made into the applanation state as the pressure of the air puff is increased, the applanation signal output from applanation sensor 2 reaches a maximum. Thereafter, cornea M becomes concave as the pressure further increases, and applanation signal voltage is reduced from the maximum.

Timing controller 26 provides the command signal every time comparator 22 is at the H-level, and A/D converter 16 converts the applanation signal every time it receives the command signal. RAM 27 stores the applanation signal at an address designated by counter 24. Since this address corresponds to the pressure of the air puff, the address at which the maximum value of the applanation digital signal is stored corresponds to the eye pressure.

Figure 4:
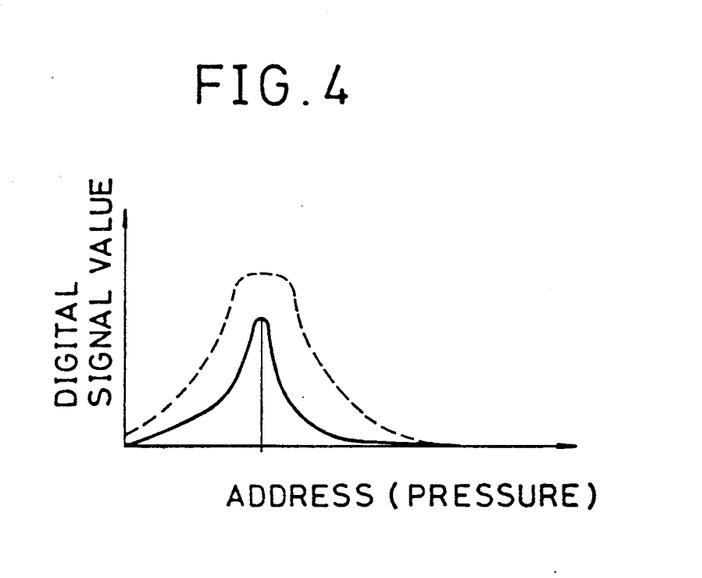
FIGS. 4 and 5 are illustrations for explaining the relation between the address of RAM and the digital signal stored therein in two different situations.

When the digital signal provided from A/D converter 16 is saturated, as shown in broken lines in FIG. 4 because the reflectance of cornea M and the applanation signal from applanation sensor 2 is too large, the signal voltage provided from alignment sensor 1 becomes large because of the large reflectance of cornea M. Therefore, the comparison reference voltage, which is the voltage that sample hold circuit 14 holds when the optical alignment is completed, becomes large. As a result, the coefficient of conversion becomes small and the digital signal provided from A/D converter 16 is controlled within a predetermined range, as shown by a solid line in FIG. 4.

Figure 5:
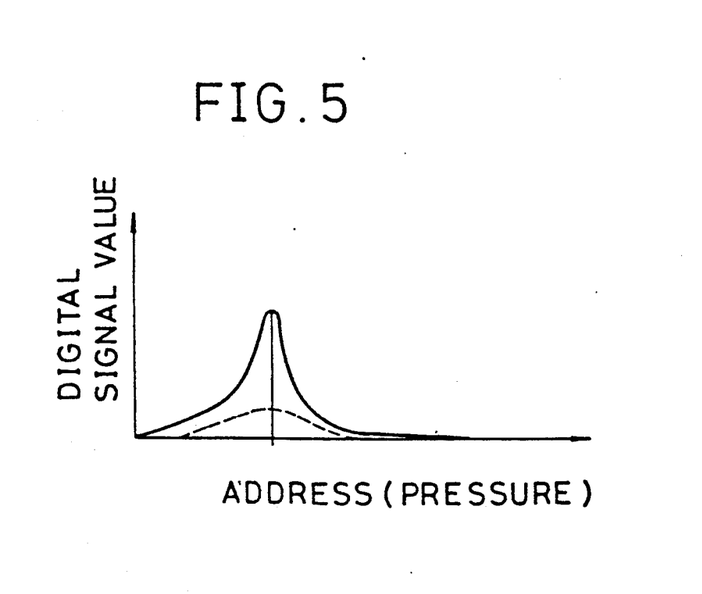

When a maximum value, as shown in broken lines in FIG. 5, of the digital signal provided from A/D converter 16 is difficult to obtain because the reflectance of cornea M and the applanation signal provided from applanation sensor 2 is too small, the signal voltage provided from alignment sensor 1 becomes small because the reflectance is small and the comparison reference voltage which is the voltage that sample hold circuit 14 holds when the optical alignment is completed, becomes small. As a result, the coefficient of conversion becomes large and the digital signal output from A/D converter 16, is held within the predetermined range as shown in a solid line in FIG. 5.

Therefore, irrespective of the degree of the reflectance of the cornea of the eye to be tested, the digital signal is controlled within a predetermined range and the correct eye pressure is measured. When a plurality of alignment detecting systems are provided, the comparison reference voltage of A/D converter 16 may be established utilizing an average value or the maximum value of the detection output of the alignment detecting systems.

Figure 6:
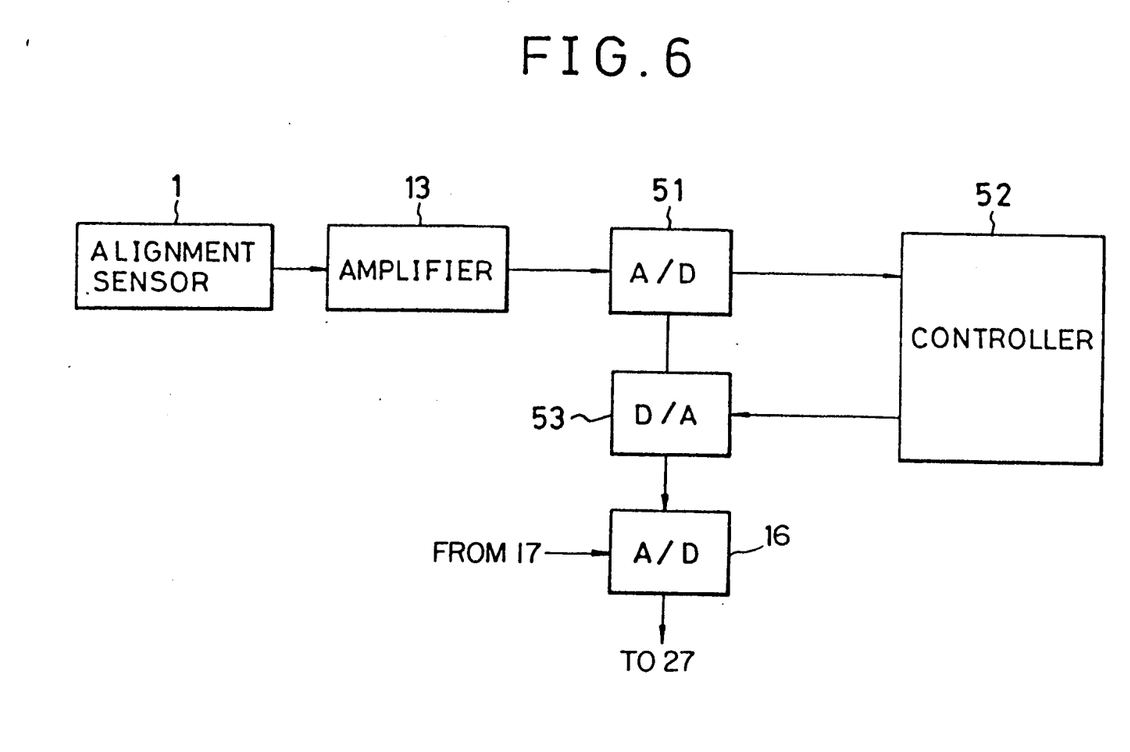
FIG. 6 is a block diagram showing a signal processing system according to a second embodiment of the present invention.
Figure 7:
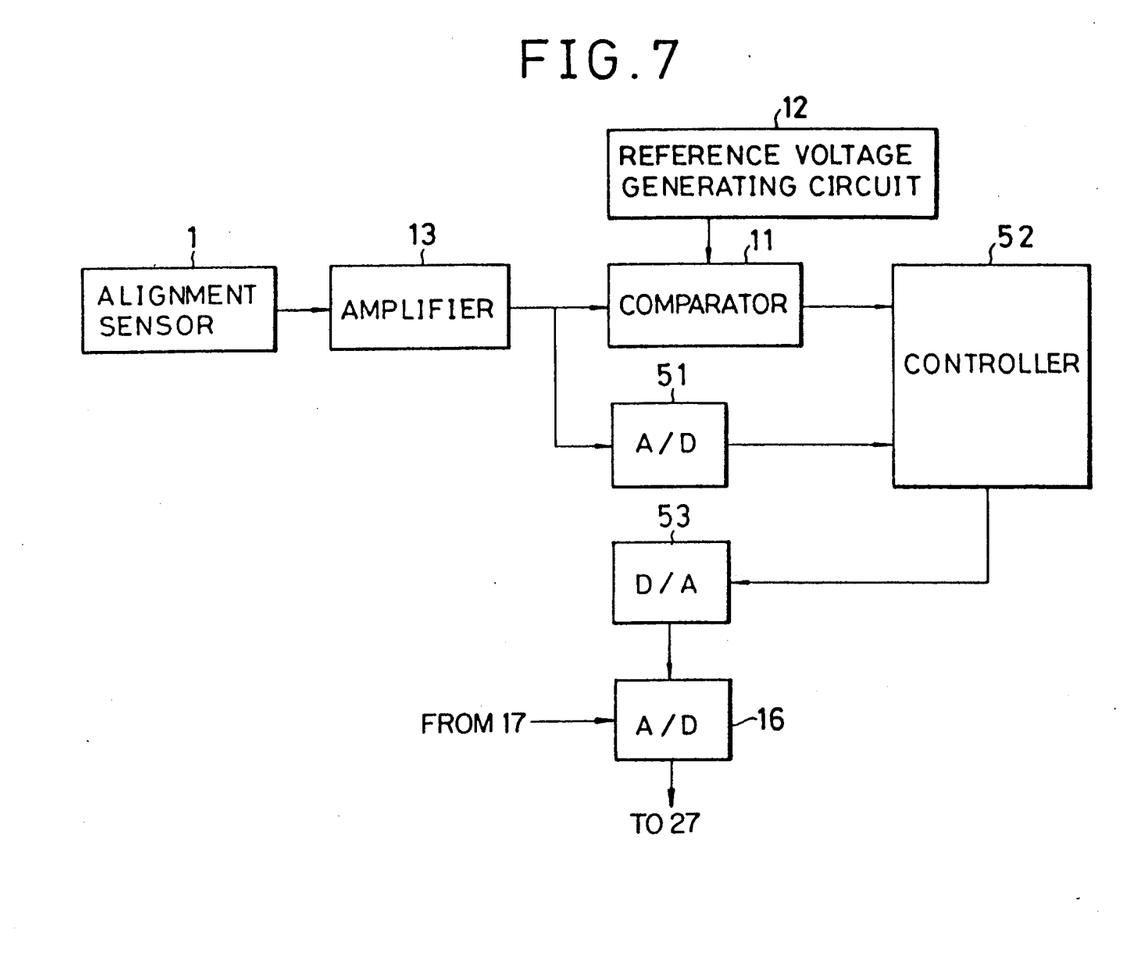
FIG. 7 is a block diagram showing a signal processing system according to a third embodiment of the present invention.

FIGS. 6 and 7 illustrate a signal processing scheme according to second and third embodiments of the present invention. In the second embodiment shown in FIG. 6, wherein elements 51-53 replace elements 11, 12, 52, 14 and 15 in the complete system of FIG. 3, the output power of alignment sensor 1 is converted to a digital signal by an A/D converter 51, without using comparator 11 as shown in FIG. 3. The alignment is detected by a controller 52 based on the converted digital signal. The digital signal is compared with a preset reference value and a comparison reference value is calculated by a controller 52. A digital signal corresponding to the calculated comparison reference value is provided to and by a D/A converter 53. The converted digital signal is provided, as a comparison reference voltage, to A/D converter 16. By this, a higher degree of correspondence is obtained irrespective of the reflectance of the cornea. Furthermore, since sample hold circuit 14 is not employed, it is not adversely affected by a continuous small amount of leakage of the hold voltage.

In the third embodiment shown in FIG. 7, wherein elements 51-53 replace elements 52, 14 and 15 in the complete system of FIG. 3, the optical alignment is detected by comparator 11 as in the first embodiment, and the remaining constitution is the same as in the second embodiment, the input and output relation of A/D converter 51 and D/A converter 53 can be changed by controller 52. For example, in the event the reflectance of the cornea is low, the possibility of judging or interpreting noise as a desired signal due to a high sensitivity of the detection system is avoided.

As described in the foregoing, according to the present invention, a stable applanation signal can always be detected irrespective of the reflectance of the cornea of the eye to be tested. Therefore, a correct and stable measurement of the eye pressure is obtained even if the reflectance of the cornea of the eye to be tested varies widely.

What is claimed is:

1. An air puff type tonometer for measuring the eye pressure of an eye, comprising:
   means for projecting a light beam toward the cornea of an eye to be tested;
   means for receiving a portion of the light beam reflected from the cornea and providing a received light signal based on the quantity of light of a received portion of the light beam;
   means for detecting optical alignment based on the received light signal;
   means for directing an air puff having a pressure to the cornea when the optical alignment is detected and detecting the pressure of the air puff;
   means for detecting an applanation state of the cornea when the pressure of the air puff applanates the cornea based on the received light signal and providing an applanation signal, the detected pressure of the air puff representing the eye pressure of an eye when the applanation state of the cornea is detected;
   means for converting the applanation signal to a digital signal based on a reference value;
   means for setting the reference value based on the received light signal.

2. An air puff type tonometer according to claim 1, wherein said reference value setting means includes means for sampling and holding the received light signal.

3. An air puff type tonometer according to claim 1, wherein said reference value setting means includes means for converting the received light signal to a digital signal and means for converting said converted digital signal to an analog signal whenever the optical alignment is detected.

4. An air puff tonometer according to claim 3, wherein said reference value setting means further includes means for comparing the received light signal with a reference value and providing a comparison signal corresponding to the result of the comparison, wherein said means for converting a converted digital signal converts the converted digital signal to the analog signal based on a provided comparison signal.

5. An air puff type tonometer according to claim 1, further comprising:
   means for storing the converted applanation signal;
   means for providing said pressure signal corresponding to the detected pressure of the air puff;
   means for comparing said pressure signal with a pressure reference value and for providing a storable comparison signal when the pressure signal is greater than the pressure reference value;
   means for designating an address of said storing means based on said storable comparison signal;
   means for providing a signal corresponding to said designated address to said comparing means as a new pressure reference value; and
   means for activating said converting means in response to said comparison signal.

6. A method for measuring the eye pressure of an eye, comprising the steps of:
   projecting a light beam toward the cornea of an eye to be tested;
   receiving reflected light from the cornea after the projected light beam is reflected therefrom and providing a received light signal based on the quantity of the projected beam received;
   detecting optical alignment based on the received light signal;

directing an air puff having a pressure to the cornea;

detecting the pressure of the air puff when the optical alignment is detected;

detecting an applanation state of the cornea when the pressure of the air puff applanates the cornea based on the received light signal and providing an applanation signal;

converting the applanation signal to a digital signal based on a reference value; and setting the reference value based on the received light signal of the alignment detecting step, said air puff pressure detecting step detecting the pressure of the air puff representing the eye pressure when the applanation state of the cornea is detected.

7. The method of claim 6, wherein said step of setting the reference value includes the substep of sampling and holding said received light signal.

8. The method of claim 6, wherein said step of setting the reference value includes the substeps of converting said light receiving signal to a digital signal and converting said converted digital signal to an analog signal whenever the optical alignment is detected.

9. The method of claim 8, further comprising the substeps of comparing the received light signal with a reference value and providing a comparison signal corresponding to the result of the comparison, wherein said converted digital signal is converted to the analog signal based on the proved comparison signal.

10. The method of claim 6, further comprising the steps of:

providing a pressure signal corresponding to the detected pressure of the air puff;

comparing the provided pressure signal with a pressure reference value for providing a comparison signal when the provided pressure signal is greater than the pressure reference value;

storing said converted applanation signal in a memory, including designating an address of said memory based on said comparison signal; and providing a new pressure reference value corresponding to said designated address for said step of comparing, wherein said step of converting the applanation signal is activated in response to said comparison signal.

* * * * *